United States Patent [19]

Kobayashi et al.

[11] Patent Number: 4,874,772

[45] Date of Patent: Oct. 17, 1989

[54] ANTIASTHMATIC AGENT

[75] Inventors: Setsuo Kobayashi, Gunma; Tsugio Nakazawa, Gunma; Yasumasa Yoshie, Gunma; Yasushi Abiko, Tokyo; Kinya Kameda, Tokyo, all of Japan

[73] Assignee: Daiichi Seiyaku Co., Ltd., Tokyo, Japan

[21] Appl. No.: 186,859

[22] Filed: Apr. 27, 1988

[30] Foreign Application Priority Data

Apr. 27, 1987 [JP] Japan .................................. 62-103727

[51] Int. Cl.$^4$ ............................................ A61K 31/44

[52] U.S. Cl. ..................................... 514/341; 514/826

[58] Field of Search ................................ 514/341, 826

[56] References Cited

U.S. PATENT DOCUMENTS 4,138,491  2/1970  Ishikawa et al. ..................... 514/341

Primary Examiner—Leonard Schenkman
Attorney, Agent, or Firm—Sughrue, Mion, Zinn, Macpeak & Seas

[57] ABSTRACT

An agent for treatment and prevention of asthma comprising 2-[2-phenyl-2-(2-pyridyl)]ethyl-2-imidazoline or a salt thereof as an active ingredient is disclosed.

2 Claims, No Drawings

ANTIASTHMATIC AGENT

FIELD OF THE INVENTION

This invention relates to an agent for treatment and prevention of asthma comprising 2-[2-phenyl-2-(2-pyridyl)]ethyl-2-imidazoline or a salt thereof as an active ingredient.

BACKGROUND OF THE INVENTION

2-[2-Phenyl-2-(2-pyridyl)]ethyl-2-imidazoline (hereinafter referred to Compound A) is known to have a hypoglycemic activity (U.S. Pat. No. 4,138,491), an inhibitory activity on blood platelet aggregation (U.S. Pat. No. 4,138,491), and a therapeutic effect on retinopathy (Japanese Patent Application (OPI) No. 194020/86 (the term "OPI" as used herein means an unexamined published Japanese patent application)), but has not been reported to have an effect for treatment of asthma.

SUMMARY OF THE INVENTION

The present inventors have found that Compound A and salts thereof exhibit excellent effects for treatment and prevention of asthma and completed the invention.

The present invention relates to an agent for treatment and prevention of asthma containing Compound A or a salt thereof as an active ingredient.

DETAILED DESCRIPTION OF THE INVENTION

The salt of Compound A includes physiologically acceptable acid addition salts formed with inorganic acids, e.g., hydrochloric acid, hydrobromic acid, etc., and organic acids, e.g., maleic acid, fumaric acid, etc.

Pharmaceutical preparations containing Compound A or a salt thereof include tablets, capsules, powders, granules, injectable solutions, suppositories, inhalants, syrups and dermal preparations. These preparations can be prepared by known pharmaceutical techniques using appropriate additives such as excepients, e.g., corn starch, lactose, etc., binders, e.g., hydroxypropyl cellulose, polyvinyl pyrrolidone, etc., disintegrators, e.g., low substituted hydroxypropyl cellulose, crystalline cellulose, etc., and lubricants, e.g., talc, magnesium stearate, etc. If desired, the preparations of the present invention can be slow release or sustained release preparations using a known preparation technique.

The asthmatic diseases, on which the preparations of the present invention are specifically effective, include bronchial asthma, cardiac asthma, and the like.

The preparations according to the present invention can be administered orally or parenterally. The dose level for oral administration usually ranges from 30 to 1200 mg/day, and preferably from 50 to 400 mg/day, for adult human (about 50 to 60 kg body weight).

Compound A and the salts thereof are of low toxicity, and $LD_{50}$ of dihydrochloride 3/2 hydrate of Compound A was found to be 1,137 mg/kg (p.o.) and 42 mg (i.v.) in male rats.

Compound A and the salts thereof have been proved to have excellent effects for prevention and treatment of asthma as illustrated in Example hereinafter described and, therefore, these compounds are useful as excellent antiasthmatic agents.

The present invention is hereinafter illustrated in greater detail with reference to Reference Example and Example, but it should be understood that these examples are not construed as limiting the present invention.

REFERENCE EXAMPLE

| | |
|---|---|
| Dihydrochloride 3/2 hydrate of Compound A | 100 mg |
| Lactose | 61 mg |
| Corn starch | 32 mg |
| Hydroxypropylmethyl cellulose | 6 mg |
| Magnesium stearate | 1 mg |
| Total | 200 mg |

The above components were mixed and compressed by a tabletting machine in a usual manner to prepare tablets each weighing 200 mg.

EXAMPLE

Dihydrochloride 3/2 hydrate of Compound A (200 mg) was administered to each of 6 patients suffering from intractable asthma and depending on steroids in a single dose after meal. Two out of the 6 patients successively received 200 mg of Compound A in three divided doses per day for consecutive one week. Before administration and after 1, 2 and 3 hours from the administration, the forced expiratory volume in one second ($FEV_1$), forced vital capacity (FVC), and peak expiratory flow (PEF) were measured with an electronic spirometer (Nihon Koden Co., Ltd., Japan) and the respiratory resistance (Rrs) was determined with Astograph-TCK-6100-H (Chest Co., Ltd., Japan). These values are indices to the antiasthmatic effects. The results obtained are shown in Table 1 below as average±standard error.

TABLE 1

| Item | Before Administration | After Administration | | |
|---|---|---|---|---|
| | | After 1 Hr. | After 2 Hrs. | After 3 Hrs. |
| $FEV_1$ (l) | 1.01 ± 0.16 | 1.08 ± 0.15 | 1.17 ± 0.16** | 1.20 ± 0.18 |
| FVC (l) | 2.06 ± 0.13 | 2.26 ± 0.18 | 2.37 ± 0.18* | 2.60 ± 0.27* |
| PEF (l) | 2.90 ± 0.28 | 2.85 ± 0.28 | 3.17 ± 0.34 | 3.19 ± 0.38 |
| Rrs (cm $H_2O$/liter/sec.) | 9.98 ± 1.32 | 8.90 ± 1.58 | 6.90 ± 1.03** | 8.05 ± 1.67* |

Note:
*The difference from the value before administration was significant at the level of 5% or less by paired t-test.
**The difference from the value before administration was significant at the level of 1% or less by paired t-test.

As is apparent from Table 1, $FEV_1$, PEF, and FVC all increased, while Rrs decreased after 2 hours from the administration of Compound A.

Further, improvements on manifestations of asthma, such as coughs, stridor, dyspnea, and the like were noted in five of the patients.

Side effects causing hypoglycemosis, such as changes of blood pressure and heart beat, tremor, anxiety, palpitation, and the like, were not observed at all in any of the 6 patients.

While the invention has been described in detail and with reference to specific embodiments thereof, it will be apparent to one skilled in the art that various changes and modifications can be made therein without departing from the spirit and scope thereof.

What is claimed is:

1. A process for treating asthma which comprises administering 2-[2phenyl-2(2pyridyl)]-ethyl-2-imidazoline in an amount effective for treating asthma to a patient in need of such treatment.

2. A process for preventing asthma which comprises administering 2-[2-phenyl-2-(2-pyridyl)]-ethyl-2-imidazoline in an amount effective for preventing asthma to a patient in need of such prevention.

* * * * *